United States Patent
Chen et al.

(10) Patent No.: US 7,262,037 B2
(45) Date of Patent: Aug. 28, 2007

(54) METHOD FOR THE PRODUCTION OF D-(-)-3-HYDROXYBUTYRIC ACID BY RECOMBINANT ESCHERICHIA COLI

(76) Inventors: Guoqiang Chen, Dept. of Biology, Tsinghua University, Beijing 100084 (CN); Jinchun Chen, Dept of Bilogical Sciences & Biotechnology, Tsinghua University, Beijing 100084 (CN); Haijun Gao, Dept of Biology, Tsinghua University, Beijing, 100084 (CN)

( * ) Notice: Subject to any disclaimer, the term of this patent is extended or adjusted under 35 U.S.C. 154(b) by 528 days.

(21) Appl. No.: 10/336,844

(22) Filed: Jan. 6, 2003

(65) Prior Publication Data

US 2003/0203459 A1  Oct. 30, 2003

(30) Foreign Application Priority Data

Jan. 4, 2002  (CN)  .......................... 2002 1 000144

(51) Int. Cl.
*C12P 7/40* (2006.01)
*C12N 1/21* (2006.01)
*C12N 15/74* (2006.01)

(52) U.S. Cl. ................. 435/136; 435/488; 435/252.33; 536/23.2

(58) Field of Classification Search ................. 435/136, 435/252.33, 488; 536/23.2
See application file for complete search history.

(56) References Cited

FOREIGN PATENT DOCUMENTS

RU        2096035 C1    11/1997
WO        WO 00/28985   5/2000

OTHER PUBLICATIONS

Choi, J.I., S.Y. Lee, and K. Han. 1998. Cloning of the *Alcaligenes latus* polyhydroxyalkanoate biosynthesis genes and use of these genes for enhanced production of Poly(3-hydroxybutyrate) in *Escherichia coli*. Appl Environ Microbiol. 64:4897-903.
Liebergesell, M., B. Schmidt, and A. Steinbuchel. 1992. Isolation and identification of granule-associated proteins relevant for poly(3-hydroxyalkanoic acid) biosynthesis in *Chromatium vinosum* D. FEMS Microbiol Lett. 99:227-32.
Liebergesell, M., and A. Steinbuchel. 1993. Cloning and molecular analysis of the poly(3-hydroxybutyric acid) biosynthetic genes of *Thiocystis violacea*. Appl Microbiol Biotechnol. 38:493-501.
Peoples, O.P., and A.J. Sinskey. 1989. Poly-beta-hydroxybutyrate biosynthesis in *Alcaligenes eutrophus* H16. Characterization of the genes encoding beta-ketothiolase and acetoacetyl-CoA reductase. J Biol Chem. 264:15293-7.
Putnoky, P., A. Kereszt, T. Nakamura, G. Endre, E. Grosskopf, P. Kiss, and A. Kondorosi. 1998. The pha gene cluster of *Rhizobium meliloti* involved in pH adaptation and symbiosis encodes a novel type of K+ efflux system. Mol Microbiol. 28:1091-101.
GenBank Accession No. AF078795. Dec. 9, 1998. *Alcaligenes latus* polyhydroxyalkanoate synthase protein PhaC (phaC), ketothiolase protein PhaA (phaA), and reductase protein PhaB (phaB) genes, complete cds.
GenBank Accession No. J04987. Apr. 24, 1993. A.eutrophus beta-ketothiolase (phbA) and acetoacetyl-CoA reductase (phbB) genes, complete cds.
GenBank Accession No. L01112. Apr. 26, 1993. *Chromatium vinosum* poly(3-hydroxybutyric acid) phbA, phbB, phbC) genes, complete cds.
GenBank Accession No. U47026. Jan. 29, 1999. *Alcaligens latus* poly(3-hydroxyalkanoate) synthesis (phaC, phaA, and phaB) genes, complete cds.
GenBank Accession No. X93358. Mar, 12, 1999. *Rhizobium meliloti* pha[A,B,C,D,E,F,G] genes.
GenBank Accession No. L01113. Jun. 26, 1996. *Thiocystis violacea* beta-ketothiolase and PHA synthase (phbA and phbC) genes, complete cds.

Primary Examiner—Chih-Min Kam
(74) Attorney, Agent, or Firm—Dykema Gossett PLLC; Gregory M. Zinkl

(57) ABSTRACT

This invention relates to a method for the production of D-(-)-3-hydroxybutyric acid, comprising the step of culturing a recombinant strain containing genes phbA, phbB, ptb and buk by fermentation. Preferably, the recombinant strain is a strain of *E. coli*. The method of the invention is simple, avoiding the technique of degrading polymer to produce D-(-)-3-hydroxybutyric acid. The present method also provides improved efficiency, lowers the complicated requirement for facilities as used in traditional chemical synthesis, simplifies the complicated technique flow, and omits the complicated chiral separation step. Therefore, the present method greatly reduces the costs associated with D-(-)-3-hydroxybutyric acid production. Also, with this invention, the problems such as environmental pollution of chemical synthesis and chiral separation are overcome.

9 Claims, 2 Drawing Sheets

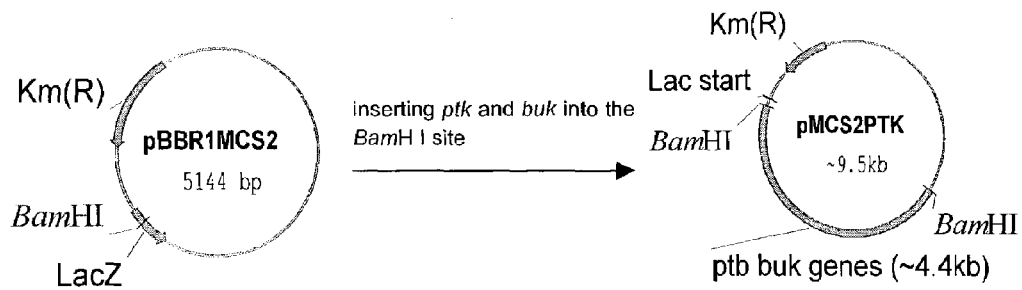
FIG. 3
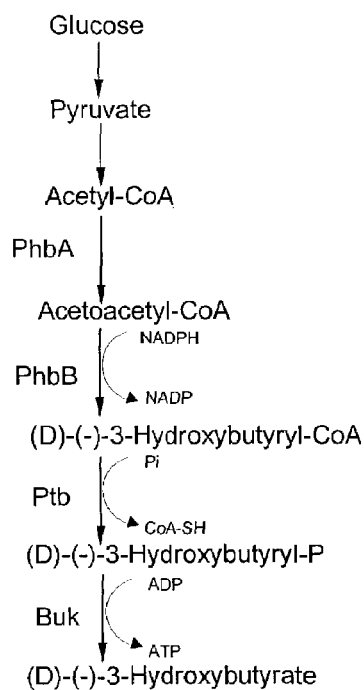
FIG. 4. Design of metabolic pathway for the extracellular production of D-(-)-3-Hydroxybutyrate. β-ketothiolase (PhbA), acetoacetyl-CoA reductase (PhbB), phosphotransbutyrylase (Ptb) and butyrate kinase (Buk) were encoded by genes phbA and phbB from Ralstonia eutropha, and genes ptu and bub from Clostridium acetobutylicum, respectively.

METHOD FOR THE PRODUCTION OF D-(-)-3-HYDROXYBUTYRIC ACID BY RECOMBINANT ESCHERICHIA COLI

FIELD OF INVENTION

This invention relates to a method for the production of D-(-)-3-hydroxybutyric acid by recombinant *Escherichia coli*.

BACKGROUNDS

D-(-)-3-hydroxybutyric acid

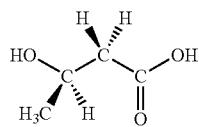

is a very valuable intermediate in fine chemical industry, which can be directly used as drug for treating various diseases (Russia Patent 2096035-C1, U.S. Pat. No. 5,112,865, WO00/28985). The traditional methods for the production of D-(-)-3-hydroxybutyric acid (3HB) are chemical synthesis, and a process involving obtaining the 3HB degrading from its polymer poly-D-(-)-3-hydroxybutyric acid (PHB) which is synthesized by bacteria. Both of these two methods relate to very complicated techniques, require a complex chiral separation process to get the target compound, and require large production input, leading to much higher costs of D-(-)-3-hydroxybutyric acid production. On the other hand, environmental pollution also exists in the process of chemical synthesis and chiral separation. Therefore, there still exists a demand for new methods for the production of D-(-)-3-hydroxybutyric acid, which methods are cost-effective and avoid the chiral separation process.

It has been known that β-ketothiolase encoded by gene phbA (or pbaA) catalyzes two acetyl-CoAs into acetoacetyl-CoA; and that acetoacetyl-CoA reductase encoded by gene phbB (or phaB) catalyzes acetoacetyl-CoA into D-(-)-3-hydroxybutyryl-CoA. The combined use of gene phbA and gene phbB in a bacteria can lead to the production of hydroxybutyryl-CoA. Gene ptb and gene buk encode phosphotransbutyrylase and butyrate kinase, respectively. Enzymes encoded by these two genes can catalyze hydroxybutyryl-CoA into D-(-)-3-hydroxybutyric acid in bacteria. Thus, the inventors attempted to use the combination of these four genes to produce D-(-)-3-hydroxybutyric add via a one-step method in engineered bacteria, and succeeded finally.

SUMMARY OF THE INVENTION

The object of the invention is to provide a new method with simple techniques and high efficiency for the production of D-(-)-3-hydroxybutyric acid. To achieve this object, the following technical solution is adopted in this invention: a method for the production of D-(-)-3-hydroxybutyric acid comprising the steps of fermenting a recombinant bacteria strain harboring phbA(or phaA), phbB(or phaB), ptb and buk genes, and purifying the resulted D-(-)-3-hydroxybutyric acid. A batch or fed-batch cultivation can be used in this invention.

DETAILED DESCRIPTION OF THE INVENTION

According to the present method, a bacterial metabolic pathway for the production of D-(-)-3-hydroxybutyric acid is designed as shown in FIG. 4. The pathway begins from glucose, passing through pyruvate, acetyl-CoA, acetoacetyl-CoA, D-(-)-3-hydroxybutyryl-CoA, D-(-)-3-hydroxybutyryl-P, and finally synthesizes D-(-)-3-hydroxybutyric acid (3HB). Genes phbA, phbB, ptb and buk are involved in this newly constructed metabolic pathway. With this metabolic pathway, D-(-)-3-hydroxybutyric acid can be produced extracellularly in one step.

According to the invention, genes phbA, phbB, ptb and buk can be cloned from various bacteria, including *Pseudomonas, Ralstonia eutropha, Alcaligenes, Chromatium, Thiocystis*, Yeast, *Clostridium, Thermobacillus*, etc. For example, the sequences of phbA and phbB can be obtained from GenBank with the following accession numbers: AF029714, AF078795, U47026, X93358, J04987, L01112, L01113, etc.; the sequence of gene ptb can be obtained from L04468, AB035092, AJ278958 (Genbank accession numbers), etc.; the sequence of buk can be obtained from L04468, AB035092 (Genbank accession numbers), etc. Preferably, gene sequences used in the present invention are J04987 and L01112 for phbA and phbB, and L04468 and AB035092 for ptb and buk, respectively.

According to the invention, the recombinant bacteria strain can be any appropriate commercial strains, preferably, an *E. coli* strain which can be JM109, HB101, DH5α, etc.

According to the method of the invention, first, genes phbA, phbB, ptb and buk are cloned into plasmids, then these constructed plasmids are used to transform the recombinant bacterial strains, and finally D-(-)-3-hydroxybutyric acid is obtained from the recombinant strain cultures. Genes phbA, phbB, ptb and buk can be cloned into one plasmid, or alternatively into more than one plasmids with random combination.

For the recombinant strain, the optimum temperature ranges between 28-42° C., and the optimum pH ranges between 5.5-8.5, depending on their different origins. The recombinant strains can be cultured in a batch process, or a fed-batch process.

The invention was designed smartly in that the techniques for plasmid construction and recombinant strain screening involved in this invention are all carried out by genetic engineering manipulations known in the art, including PCR amplification, restriction enzyme digestion, ligation by ligase, plasmid transformation, screening and cultivation of the recombinant strain, as well as confirmation of the plasmid constructs and purchase of the recombinant commercial strain. There is no need to purchase new facilities for fermentation, and rather, routine industrial fermentation facilities can finish the desired production process.

The recombinant strains are creatively used in the invention for fermentation, which allow a one-step method for D-(-)-3-hydroxybutyric acid production. The method of the invention is simple, avoiding the technique of degrading polymer to produce D-(-)-3-hydroxybutyric acid. The present method also provides improved efficiency, lowers the complicated requirement for facilities as used in traditional chemical synthesis, simplifies the complicated technique flow, and omits the complicated chiral separation step. Therefore, the present method reduces the costs associated with D-(-)-3-hydroxybutyric acid production to the full extent. Also, with this invention, the problems such as environmental pollution of chemical synthesis and chiral separation are overcome.

The invention is described below in more detail with reference to the examples and drawings.

DESCRIPTION OF DRAWINGS

FIG. 3 shows the construction of plasmid pMCS2PTK.

FIG. 4 shows the design of metabolic pathway in recombinant microbes for the production of D-(−)-3-hydroxybutyric acid according to the invention.

EXAMPLE 1

The Construction of the Recombinant *E. coli*

Strain: *E. coli* HB101

Figure 1:
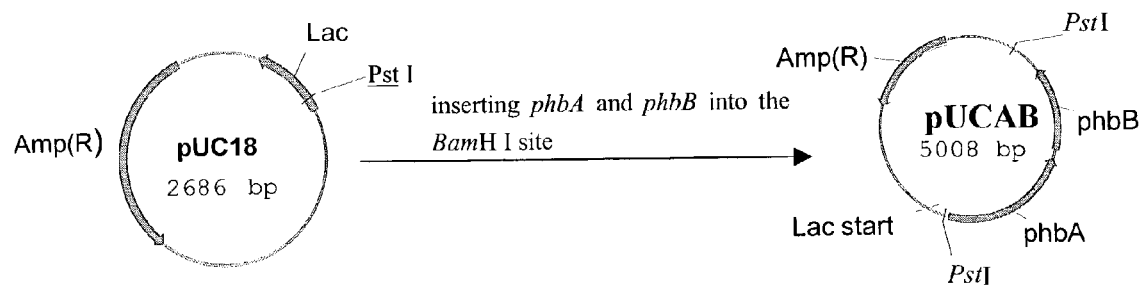
FIG. 1 shows the construction of plasmid pUCAB.

Plasmid Construction:

1. As shown in FIG. 1, genes phbB and phbA were inserted into plasmid vector pUC18. The resulting plasmid pUCAB contained genes phbB and phbA downstream the lac promotor.

The plasmid was selected on Medium 1 which medium contains 10 g/l peptone, 5 g/l yeast extract, 10 g/l NaCl, 10 g/l glucose, and 60 µg/L ampicillin.

Figure 2:
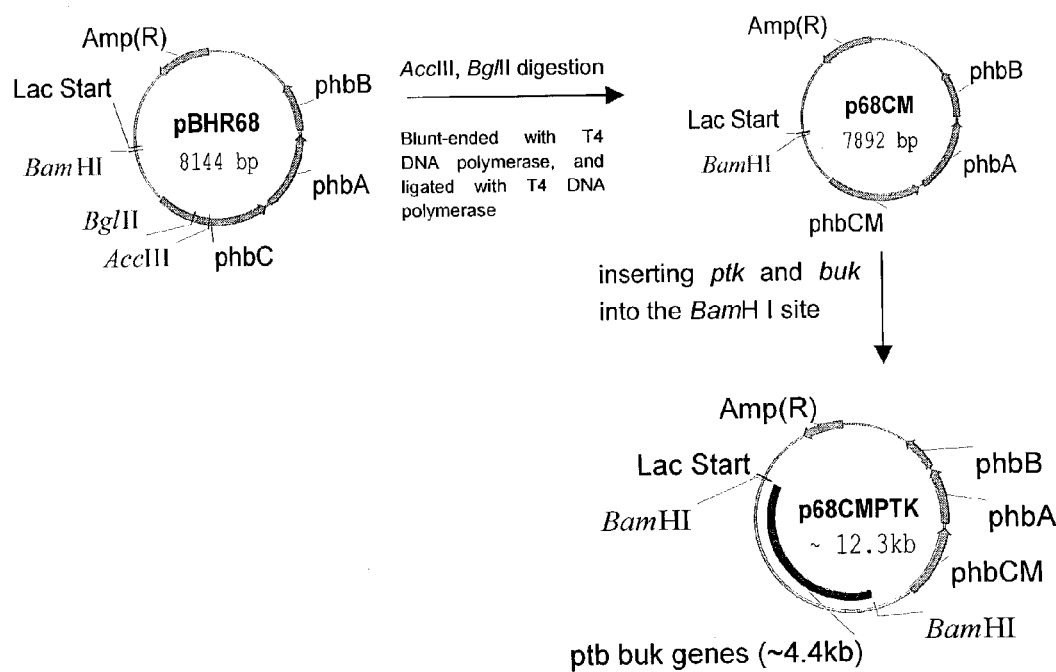
FIG. 2 shows the construction of plasmid p68CMPTK from plasmids pBHR68CM and pJC7.

2. As shown in FIG. 2, plasmid pBHR68 containing operon phbCAB was digested with AccIII and BglII, blunted with T4 DNA polymerase and further ligated with T4 DNA ligase to give plasmid pBHR68CM. Genes ptb and buk were inserted into BamHI-digested plasmid pBHR68CM to construct plasmid p68CMPTK. Genes ptb and buk are obtained from, e.g. plasmid pJC(Cary J. W., etc, J. Bacteriol 170, 4613-4618) with restriction enzyme BamHI.

Medium 2 was used to select the plasmids just mentioned above which medium contains 0.5 g/L $(NH_4)_2SO_4$, 0.2 g/L $MgSO_4$, 9.65 g/L $NaHPO_4 \cdot 12H_2O$, 2.65 g/L $KH_2PO_4$, 60 µg/L ampicillin and/or 50 µg/L kanamycin, 1 ml/L microelement solution (in 1 mol/L HCl(g): 20 $FeCl_3 \cdot 6H_2O$, 10 $CaCl_2$, 0.03 $CuSO_4 \cdot 5H_2O$, 0.05 $MnCl_2 \cdot 4H_2O$, 0.1 $ZnSO_4 \cdot 7H_2O$). The types and concentrations of carbon sources and organic nitrogen sources were determined as desired.

3. As shown in FIG. 3, plasmid pJC7 was digested with BamHI to obtain a fragment containing buk and ptb genes. Then, the fragment was inserted into plasmid pBBR1MCS2 (kindly provided by P&G Corporation, U.S.A) to obtain plasmid pMCS2PTK harboring genes of ptb and buk.

Medium 3 was used to select the plasmid as mentioned above which medium contains 4 g/L $KH_2PO_4$, 4 g/L $K_2HPO_4$, 12 g/L $Na_2HPO_4 \cdot 12H_2O$, 0.5 g/L $NH_4Cl$, 1.2 g/L $(NH_4)_2SO_4$, 2.2 g/L $MgSO_4 \cdot 7H_2O$, 9.65 g/L $NaHPO_4 \cdot 12H_2O$, 2.65 g/L $KH_2PO_4$, 60 µg/L ampicillin and/or 50 µg/L kanamycin, 1 ml/L microelement solution (in 1 mol/L HCl(g): 20 $FeCl_3 \cdot 6H_2O$, 10 $CaCl_2$, 0.03 $CuSO_4 \cdot 5H_2O$, 0.05 $MnCl_2 \cdot 4H_2O$, 0.1 $ZnSO_4 \cdot 7H_2O$). The types and concentrations of carbon sources and organic nitrogen sources were determined according to growth requirement.

Plasmid transformation: Electrotransformation or chemical transformation was used to transform the plasmids into strain *E. coli*.

In this example, in addition to *E. coli* HB101, the *E. coli* strain can also be selected from JM109, DH5α, or wild type strains such as AB1157 etc. Genes phbA and phbB could also be obtained from L01112 (GenBank Aceession Number). Genes ptb and buk could be from some other sources as well. The methods and steps to construct genetic recombinant stains were similar.

EXAMPLE 2

This example demonstrates the synthesis of D-(−)-3-hydroxybutyric acid by recombinant *E. coli* in a fed-batch fermentation process under high temperature and low pH, using glucose as carbon source.

Strain: Recombinant *E. coli* containing a single plasmid, such as plasmid p68CMPTK as prepared in Example 1.

Plasmid transformation method: chemical transformation.

Culture temperature: 42° C.

Medium: Medium 2 pH: 5.5

Aeration: 3L/3L medium/min

Fermentation time: 36 hours

Stirring speed: 150~900 rpm

A fermentor containing sterilized broth was inoculated by a seed culture in an volume of 10%. The concentration of glucose was 40 g/L. Fermentation began with a stirring speed of 150 rpm and dissolved oxygen was set at 10%. Along with the growth of the cells, stirring speed was automatically increased until reaching 900 rpm, while the dissolved oxygen kept over 10% all the time. After fermentation, cells were centrifuged, and washed. The dry weight of cells and the yield of D-(−)-3-hydroxybutyric acid and other relative data were measured and analyzed.

The yield of D-(−)-3-hydroxybutyric acid was 12 g/L after a 36-hour fermentation.

EXAMPLE 3

In this example, sucrose was used as carbon source and peptone as organic nitrogen source to synthesize D-(−)-3-hydroxybutyric acid by recombinant *E. coli* via a constant, continuous fed-batch fermentation under low culture temperature and high pH.

Strain: Recombinant *E. coli* containing two plasmids.

Plasmid transformation method: electrotransformation.

Culture temperature: 28° C.

Medium: Medium 3 pH: 8.5

Aeration: 2L/3L medium/min

Fermentation time: 48 hours

Stirring speed: 150~900 rpm

A seed culture was inoculated into a fermentor containing sterilized broth with in a volume of 10%. The concentration of beef extract was 10 g/L. The initial concentration of sucrose was 30 g/L. Fermentation began with a stirring speed of 150 rpm. The dissolved oxygen was controlled over 10% by adjusting the agitation. The concentration change of sucrose was monitored on-line during fermentation. When the sucrose concentration was consumed to reach 10 g/L, substrate was fed with controlled flow rate. After the feeding was finished, the cultivation was continued until the entire carbon source was exhausted. After fermentation, cell dry weight, yield of D-(−)-3-hydroxybutyric acid, and other relative data were analyzed.

The yield of D-(−)-3-hydroxybutyric acid was 25 g/L after a 48-hour fermentation.

EXAMPLE 4

In this example, glycerol was used as carbon source to synthesize D-(−)-3-hydroxybutyric acid by recombinant *E. coli* in a fed-batch fermentation with constant dissolved oxygen.

Strain: Recombinant *E. coli* JM 109 containing two plasmids, in which the gene was phbA (AF078795), phb B (L04468), ptb (AJ278958) and buk (AB035092).

Plasmid transformation method: electrotransformation.

Culture temperature: 35° C.

Medium: Medium 3 pH: 7.0

Aeration: 2L/3L medium/min

Fermentation time: 52 hours

Stirring rate: 150~900 rpm

A seed culture was inoculated into a fermentor containing sterilized broth in a volume of 10%. No organic nitrogen was added in the broth. The initial concentration of glycerol was 20 g/L. Fermentation began with a stirring rate of 150 rpm and the dissolved oxygen was controlled over 10% by automatic adjusting the agitation. The agitation decreased when the glycerol was exhausted. Then the stirring speed was kept as 200 rpm, and the dissolved oxygen was controlled at about 10% by feeding glycerol. When the feeding was finished, cultivation was continued until the carbon source was exhausted. After fermentation, cell dry weight, yield of D-(−)-3-hydroxybutyric acid, and other relative data were analyzed.

The yield of D-(−)-3-hydroxybutyric acid was 22 g/L after a 52-hour fermentation.

The invention claimed is:

1. A method of producing D-(−)-3-hydroxybutyric acid comprising the steps of:
    (a) cloning genes phbA, phbB, ptb and buk into plasmids to construct new plasmids;
    (b) transforming the constructed plasmids into a bacterial strain to construct a recombinant strain; and
    (c) culturing the recombinant strain under conditions to produce D-(−)-3 hydroxybutryic acid,
    wherein the sequences of genes phbA and phbB are selected from the group consisting of GenBank Accession Numbers AF029714, AF078795, U47026, X93358, J04987, L01112, and L01113; the sequence of gene ptb is selected from the group consisting of L04468, AB035092, and AJ278958; and the sequence of gene buk is L04468 or AB035092.

2. The method of claim 1, wherein the recombinant strain is *E. coli*.

3. The method of claim 2, wherein the *E. coli* strain is selected from the group consisting of JM109, HB101, DH5α and wild-type strains.

4. The method of claim 1, wherein one plasmid comprises the phbA, phbB, ptb and buk genes.

5. The method of claim 1, wherein more than one plasmid comprise the phbA, phbB, ptb and buk genes.

6. The method of claim 1, wherein the recombinant strain is cultured at 28 to 42° C.

7. The method of claim 1, wherein the recombinant strain is cultured at a pH ranging of 5.5 to 8.5.

8. The method of claim 1, wherein the recombinant strain is cultured by a batch process.

9. The method of claim 1, wherein the recombinant strain is cultured by a fed-batch process.

* * * * *

UNITED STATES PATENT AND TRADEMARK OFFICE
CERTIFICATE OF CORRECTION

PATENT NO. : 7,262,037 B2 Page 1 of 1
APPLICATION NO. : 10/336844
DATED : August 28, 2007
INVENTOR(S) : Guoqiang Chen, Jinchun Chen and Haijun Gao It is certified that error appears in the above-identified patent and that said Letters Patent is hereby corrected as shown below:

On the Title Page
At Item (30) on the face of the patent, "Foreign Application Priority Information":

Delete "2002 1 000144" and replace with -- 02100014.X --

Signed and Sealed this

Fourth Day of December, 2007

JON W. DUDAS
*Director of the United States Patent and Trademark Office*